United States Patent
Fabiani et al.

(12) 
(10) Patent No.: US 6,589,277 B1
(45) Date of Patent: Jul. 8, 2003

(54) FLANGED PROSTHESIS

(75) Inventors: Jean Noël Fabiani, Paris (FR); Rachid Zegdi, La Garenne Colombes (FR)

(73) Assignee: Laboratoire Perouse Implant, Bornel (FR)

( * ) Notice: Subject to any disclaimer, the term of this patent is extended or adjusted under 35 U.S.C. 154(b) by 0 days.

(21) Appl. No.: 09/685,581

(22) Filed: Oct. 11, 2000

(30) Foreign Application Priority Data

Oct. 11, 1999 (FR) ............................................ 99 12642

(51) Int. Cl.⁷ .................................................. A61F 2/06
(52) U.S. Cl. ........................ 623/1.31; 623/1.36; 606/153
(58) Field of Search .............. 604/8; 606/153, 606/154, 155; 623/1.36, 1.28, 1.29, 1.5, 1.51, 1.31

(56) References Cited

U.S. PATENT DOCUMENTS

| | | | |
|---|---|---|---|
| 3,108,357 A | * 10/1963 | Liebig | 623/1.5 |
| 3,633,585 A | * 1/1972 | McDonald, Jr. | 604/8 |
| 4,352,358 A | * 10/1982 | Angelchik | 606/155 |
| 4,854,316 A | * 8/1989 | Davis | 604/8 |
| 5,456,714 A | * 10/1995 | Owen | 604/8 |
| 5,893,886 A | * 4/1999 | Zegdi et al. | 606/153 |
| 2001/0012962 A1 | * 8/2001 | Schmitt et al. | 623/1.31 |

FOREIGN PATENT DOCUMENTS

EP 0 824 012 A1 2/1998

* cited by examiner

*Primary Examiner*—Paul B. Prebilic
(74) *Attorney, Agent, or Firm*—Wenderoth, Lind & Ponack, L.L.P.

(57) ABSTRACT

A flanged prosthesis (10) comprises a tubular body (18) equipped at one end with an external flange (19) designed for the anastomosis of the prosthesis to a tubular duct equipped with an opening. The flange (19) is made of a textile material and comprises at least one seam (324, 360, 362) shaping it at the end of the tubular body (18).

4 Claims, 5 Drawing Sheets

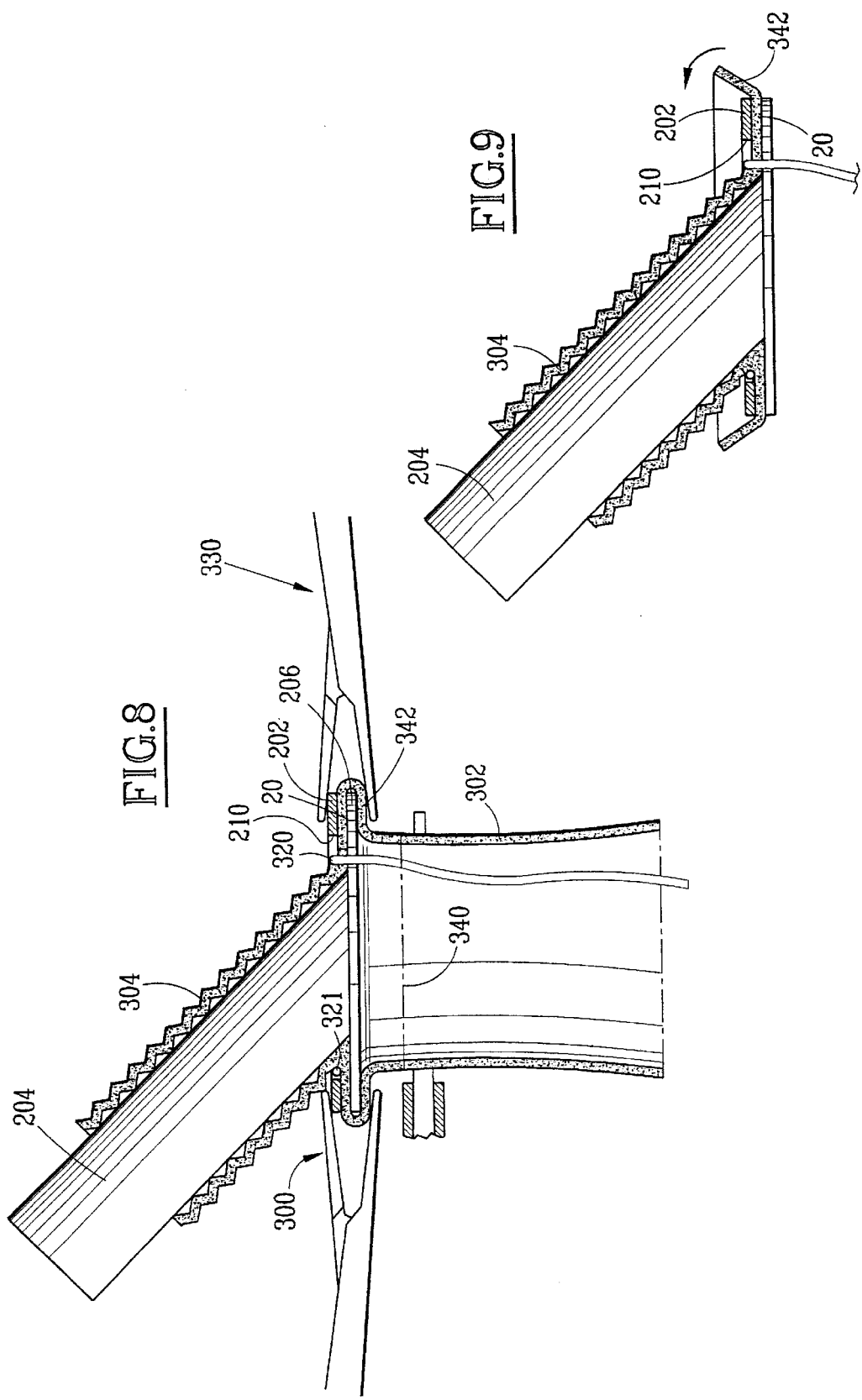

FLANGED PROSTHESIS

BACKGROUND OF THE INVENTION

The present invention relates to a flanged prosthesis of the type comprising a tubular body equipped at one end with an external flange designed for the anastomosis of the prosthesis to a tubular duct equipped with an opening.

It also relates to a method for manufacturing such a flanged prosthesis.

Flanged prostheses of this type are used as vascular prostheses, in vascular surgery, to treat unhealthy blood vessels, particularly portions of arteries, by shunting or by substitution.

As illustrated in document FR-A-2,751,867 describing a prosthesis such as this, these prostheses are connected to a tubular organic duct such as a vein or an artery, facing an opening formed in this duct.

The flange, which is at the end of the tubular body, allows the prosthesis to be attached using plastically or elastically deformable clips or staples.

The flanged prosthesis described in document FR-A-2,751,867 is made either by thermoforming its end portion or alternatively by bonding or welding a separate attached flange to the end of the tubular body.

That document tackles only the technologies that can be employed, without giving a precise description of the actual methods of manufacturing this flanged prosthesis.

Thus it is very awkward, using these technologies, to produce in a simple way a flanged prosthesis whose structure is satisfactory and which can be implanted reliably in the human body.

SUMMARY OF THE INVENTION

The object of the invention is to provide a flanged prosthesis which can be manufactured on an industrial scale and which has satisfactory reliability for durable implantation in the human body, and a method for manufacturing it.

To this end, the subject of the invention is a flanged prosthesis of the aforementioned type, characterized in that the flange is formed of a textile material and comprises at least one seam which shapes it at the end of the tubular body.

According to particular embodiments, the prosthesis comprises one or more of the following features:

the flange comprises a first ring secured, around its interior contour (surface), to the end of the tubular body, and a second ring surrounding the tubular body and running roughly against the first ring, these rings being joined together around their exterior contours (surfaces);

the first ring is connected to the tubular body by an interior first peripheral seam, and the first and second rings are joined together by an exterior peripheral seam;

the first and second rings are formed integrally with the tubular body, a peripheral fold line being formed between the first and second rings, and the second ring comprises at least one transverse seam;

the first ring comprises at least one transverse seam;

at least one of the seams runs roughly radially;

the second ring comprises two seams running radially on each side of the tubular body, roughly along one and the same diameter of the second ring; and the first ring comprises a radial single seam running roughly at right angles to the diameter along which the radial seams formed on the second ring run.

A further subject of the invention is a method for manufacturing a flanged prosthesis of the type comprising a tubular body equipped at one end with an external flange designed for the anastomosis of the prosthesis to a tubular duct equipped with an opening, characterized in that it comprises the following steps:

manufacturing a tubular portion intended to form the tubular body;

manufacturing first and second roughly flat annular elements from a textile material, the first and second elements having roughly identical exterior contours;

sewing the first annular element to one end of the tubular portion using a peripheral seam formed along the interior contour of the first annular element; and sewing the first and second annular elements together along a peripheral seam formed along their exterior contours.

As an alternative, the method comprises the following steps:

manufacturing a precursor prosthesis from textile material, comprising a tubular skirt, from one end of which at least one tubular arm intended to form the tubular body of the prosthesis emerges, the diameter of the tubular skirt being greater than the diameter of the arm, folding the tubular skirt back on itself around the tubular arm to form a first ring extending the tubular body and a second ring extending the first ring and running around the tubular body, and making at least one seam in the second ring so as to reduce its internal circumference and thus form the flange which consists of the first and second rings.

Advantageously, the step of folding the tubular skirt back on itself is performed around a rigid form comprising at least one disc-shaped part around which the flange is made.

BRIEF DESCRIPTION OF THE DRAWINGS

The invention will be better understood from reading the description which will follow which is given merely by way of example and made with reference to the drawings in which:

FIGS. 8 and 9 are side views in section illustrating the next steps in the method of manufacturing the second embodiment of the prosthesis;

DETAILED DESCRIPTION OF THE INVENTION

Figure 1:
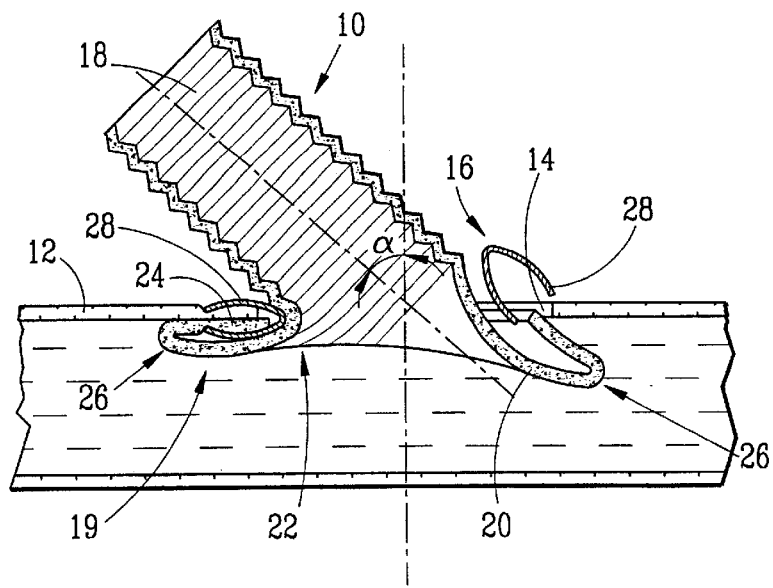
FIG. 1 is a view in longitudinal section of a flanged prosthesis in the process of being implanted.
Figure 2:
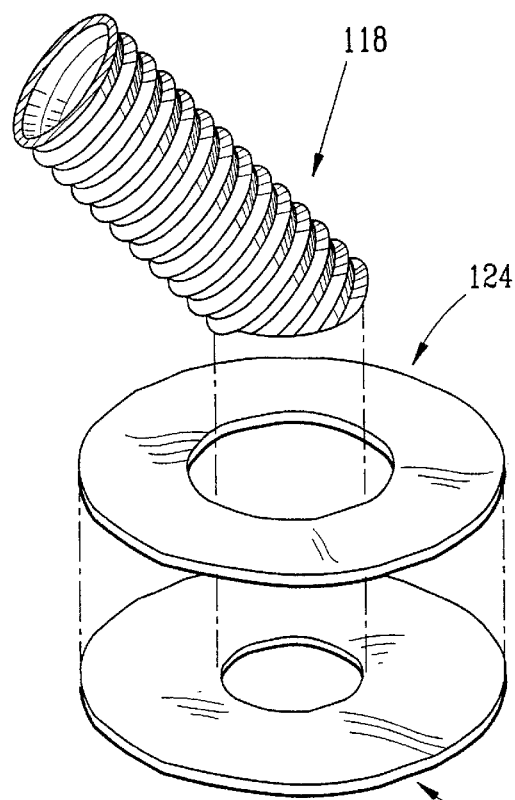
FIG. 2 is an exploded perspective view of a first embodiment of a flanged prosthesis according to the invention.

FIG. 1 generally depicts a flanged prosthesis 10 in the process of being implanted in a tubular duct 12 such as an artery. This duct is equipped, in its side wall, with an opening 14, to the periphery of which the prosthesis 10 is connected by fixing means 16.

The prosthesis 10 comprises a flexible tubular body 18 and an end flange 19.

The body 18 consists of a ringed tubular duct, that is to say one which over most of its length has a permanent helically-shaped deformation. This type of deformation is also known by the name of "lugging".

At its connection end bearing the flange 19, the tubular body 18 is extended by a first ring 20. The axis of the first ring 20 makes an angle a roughly equal to 45° with the axis of the tubular body 18.

The body 18 and the first ring 20 are joined together along the interior contour, labelled 22, of the first ring.

A second ring 24 extends the first ring 22. This is roughly pressed against the face of the first ring 20, extending the exterior surface of the body 18. It thus surrounds the end of the body 18.

The first and second rings are connected along their exterior contour 26 and together form the flange 19.

As illustrated in FIG. 1, the means 16 for connecting the flanged prosthesis to the tubular pipe 12 comprises a collection of clips 28 engaged through the opening 14 and bearing, on the one hand, against the exterior surface of the tubular duct 12 and, on the other hand, against the second ring 24, thus pressing this second ring flat against the interior surface of the tubular duct 12.

According to a first method of manufacturing the flanged prosthesis, this is made by sewing three initially separate knitted elements together.

A tubular portion 118 is designed to form the tubular body 18 of the prosthesis. A flat annular first element 120 is intended to form the first ring 20, while a flat annular second element 124 is designed to form the second ring 24.

The tubular portion 118 consists of a seamless knitted duct made, for example, by knitting polyester threads on an appropriate machine.

After knitting, this knitted portion undergoes a shaping stage known per se in order to define, over its entire length, a helically-shaped permanent deformation. The portion 118 is thus ringed.

The portion 118 is cut off at an angle at its connection end along an inclined plane which makes an angle of roughly 45° to its longitudinal axis.

The annular elements 120 and 124 are cut from pieces of fabric which are knitted with a thread of the same kind as the one used for the portion 118 and with a similar stitch. They have a slightly elliptical exterior shape.

The annular elements 120 and 124 have identical exterior contours corresponding to the desired exterior contour of the flange 19 of the prosthesis. The interior section of the annular element 124 intended to form the second ring 24 is slightly greater than the interior section of the annular element 120 intended to form the first ring 20. The interior section of the element 120 is roughly identical to the elliptical section of the angled end of the tubular element 118.

Figure 3:
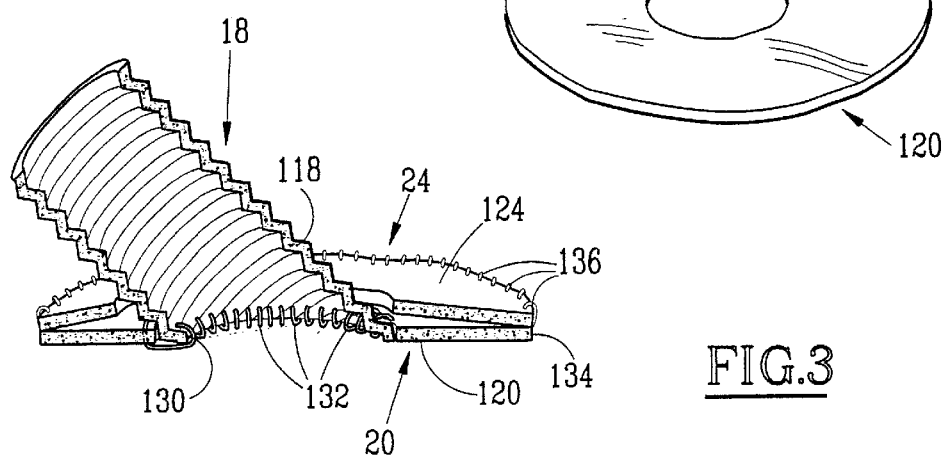
FIG. 3 is a view in perspective and in section of the flanged prosthesis of FIG. 2, assembled.

As illustrated in FIG. 3, in order to assemble the prosthesis, the angled end of the portion 118 is connected by a peripheral seam 130 around the interior contour 132 of the annular element 120 to form the first ring 20. Likewise, the exterior contour 134 of the annular element 120 is connected by a peripheral seam 136 to the annular element 124 to form the second ring 24 of the prosthesis. The annular element 124 is sewn to the first ring 20 while it is engaged around the tubular portion 118 which forms the body 18.

The prosthesis thus formed is coated with collagen so that it can be implanted in a living organism.

It will be appreciated that the prosthesis thus produced has satisfactory flexibility and that it is well tolerated by the organism. In addition, making it by sewing allows it to be made at a reasonable cost.

Figure 4:
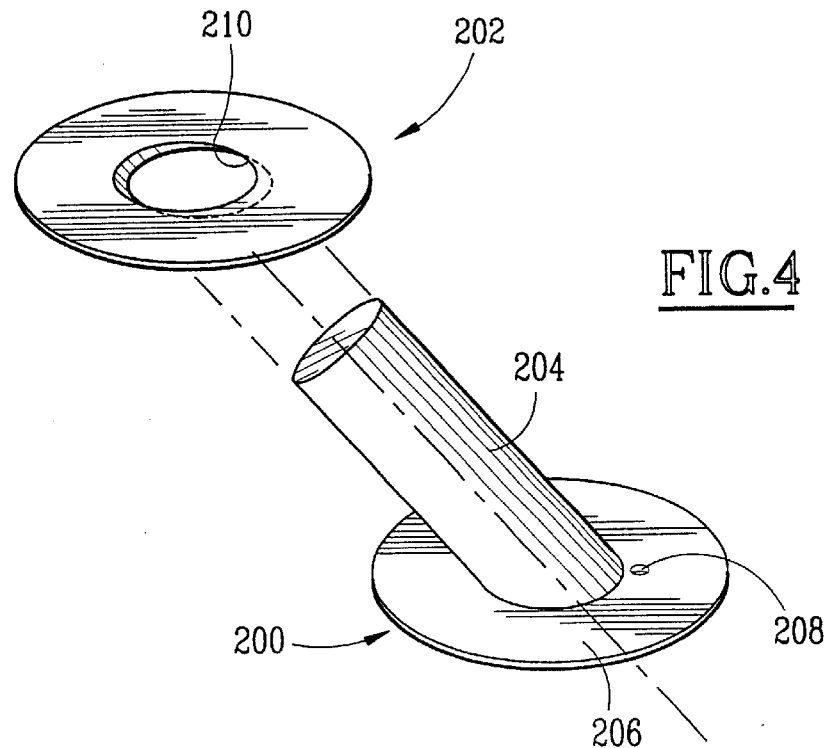
FIG. 4 is a perspective view of a tool for manufacturing a second embodiment of a flanged prosthesis according to the invention.

FIG. 4 depicts a tool for manufacturing a flanged prosthesis according to the invention by implementing another method of manufacture.

This tool comprises a tool body 200 and a washer 202. These two elements are made of metal.

The tool body comprises a straight rod 204, to one end of which an elliptical disc 206 is attached. The end of the rod 204 carrying the disc is angled at 45° so that the axis of the disc 206 makes an angle of close to 45° with the axis of the rod 204. The axis of the rod 204 passes roughly through the center of the elliptical disc 206. The axis of the rod 204 is projected orthogonally onto the disc 206 along the major axis of the disc.

An emerging hole 208 passes through the disc 206. This hole is formed at the base of the straight rod 204 along the major axis of the ellipse on the side where the rod 204 makes a maximum angle of 135° with the disc 206.

The washer 202 has an elliptical overall shape. Its exterior contour corresponds to the contour of the elliptical disc 206.

Passing through the center of the washer is an elliptical aperture 210, the section of which is slightly greater than the section of the straight rod 204 taken on a plane parallel to the disc 206. The side wall of the aperture 210, defined in the thickness of the washer 202, is angled as a cylindrical envelope to correspond to the inclination of the rod 204.

Thus, the rod 204 can be introduced into the aperture 210, thus allowing the washer 202 to slide along the length of the rod 204, remaining parallel to the disc 206. In its extreme position, the washer 202 presses precisely across the so-called upper surface of the elliptical disc 206.

Figure 5:
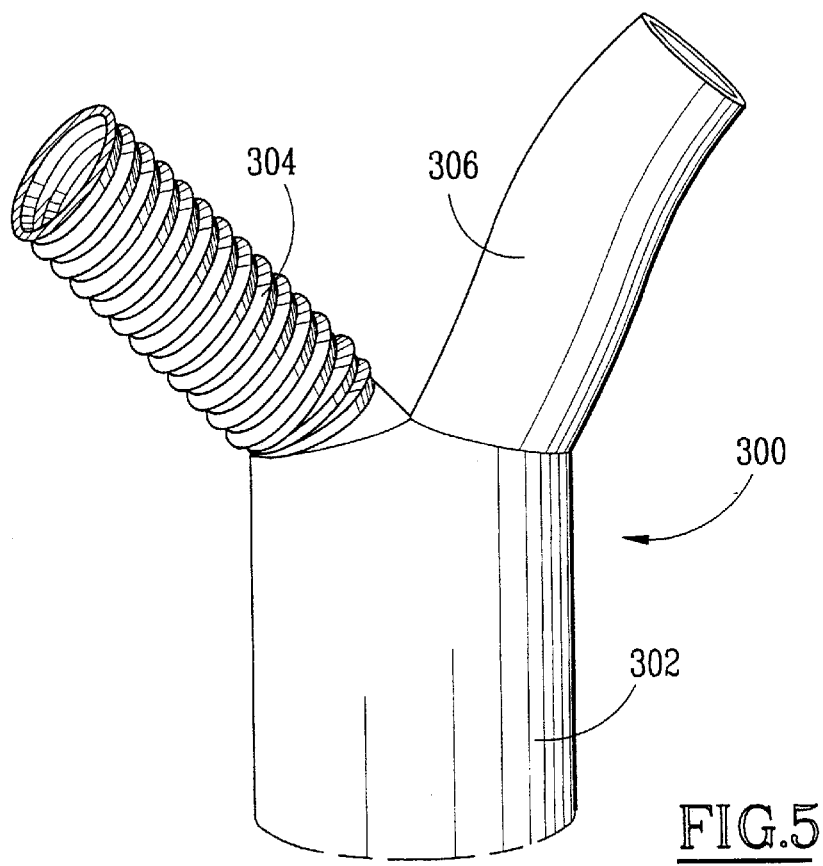
FIG. 5 is a perspective view of a vascular prosthesis preform used to manufacture the second embodiment of the flanged prosthesis.

In order to produce the prosthesis according to this second method of manufacture, use is made of a precursor depicted in FIG. 5. This consists of a forked vascular prosthesis 300. This prosthesis is normally used to connect a main section to two bypass sections. It thus has the overall shape of a Y.

This forked prosthesis is produced by knitting according to a method known per se. It comprises a main tubular body defined by a tubular skirt 302 with a diameter of about 3 cm. The body is extended by two adjacent arms 304, 306. These are formed by tubular ducts emerging side by side at one end of the body. Each tubular duct has a diameter roughly equal to half the diameter of the skirt 302.

One of the arms 304 is ringed by implementing a method known per se. By contrast, the skirt 302 and the arm 306 are smooth, these having undergone no prior shaping treatment.

Figure 6:
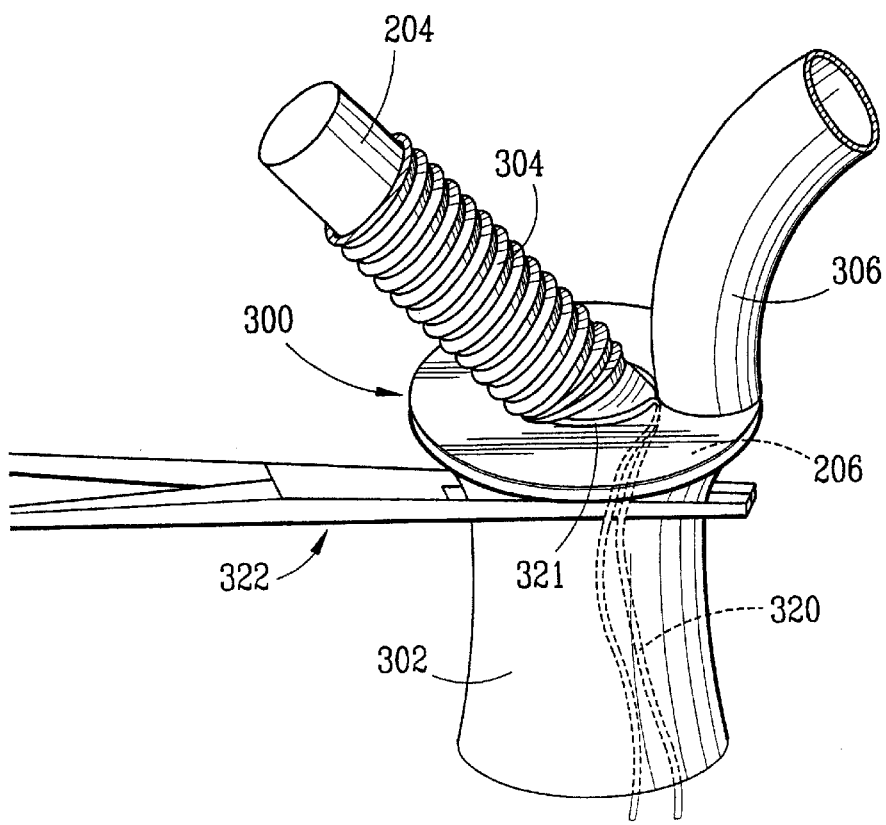
FIGS. 6 and 7 are perspective side views illustrating two successive steps in the method of manufacture of the second embodiment of the prosthesis.
Figure 7:
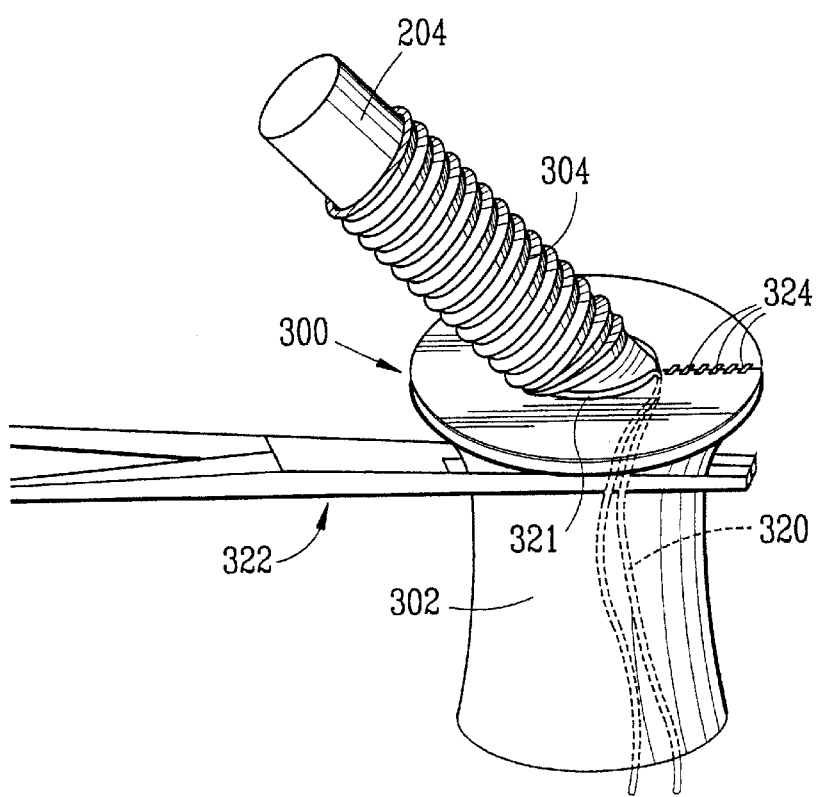

To manufacture the prosthesis and as illustrated in FIG. 6, the tool body 200 is first of all introduced into the precursor 300 from the open end of the skirt delimiting the main body. More precisely, the rod 204 of the tool body is engaged through the arm 304, the elliptical disc 206 being placed in the region where the skirt 302 meets the arms 304 and 306. In particular, the end of the arm 306 is pressed against the upper face of the elliptical disc 206 in the plane containing the hole 206, that is to say in the region of the disc delimiting the maximum angle with the axis of the rod 204.

The cylindrical wall of the skirt 302 is applied to the upper surface of the elliptical disc 206. To ensure that the skirt 302 is pressed satisfactory against the upper surface of the disc 206, a thread 320 forming a loop is engaged around the base of the arm 304 carried by the rod 204, the two lengths of the thread being introduced into the hole 206. These thus pass through the preform 300 in the region of connection of the arms 304 and 306. The two ends of the thread thus run along inside the skirt 302 and emerge at its open end. Pulling on the two ends of the thread makes sure that the skirt 302 comes into close contact with the entire upper surface of the disc 206, thus creating a peripheral fold line 321 at the end of the arm 304.

To hold the assembly in place, a clamp 322 is placed transversely around the entire width of the skirt 302. This is arranged above the disc 206, thus pulling on that part of the skirt 302 surrounding the disc 206.

In the next step, the arm 306 is cut in the plane of the disc 206 and the two edges thus defined at the end of the skirt 302 are brought together by a hand-stitched seam 324. The annular region thus delimited in the skirt 302 on the upper face of the elliptical disc 206 forms the first ring 20 of the prosthesis. The seam 324 runs radially along this ring.

In the next step illustrated in FIG. 8, the washer 202 is engaged around the arm 304 carried by the rod 204. This washer is brought to bear against the first ring 20 resting on the upper surface of the elliptical disc 206. Clamps 330 are fitted to press the washer 202 onto the first ring 20. For this purpose, one of the jaws of each clamp presses against the washer 202, while the other jaw presses against the part of the skirt 302 resting against the underside of the elliptical disc 206.

While the skirt 302 is thus held on each side of the disc 206, the standing part of the skirt 302, which forms an access length, is cut off roughly along the cutting line 340. This cutting line is formed in a position such that on the underside of the disc 206 there remains an annular layer 342 of a width, measured radially, which is roughly constant around its entire periphery. This width is roughly equal to or slightly smaller than that of the first ring 20 kept compressed between the upper surface of the disc 206 and the washer 202.

The prosthesis precursor thus supported by the tool is subjected to a stream of steam and raised to a temperature of 120° C. for 20 minutes. At the end of this treatment, the shape of the prosthesis precursor imposed by the tool supporting it is set by the action of the heat on the polyester fibres of which the knitted prosthesis is made.

Once the clamps 322 and 330 have been removed, the layer 342 which was initially facing the underside of the disc 206 is turned up and folded down onto the washer 202, still pressed against the first ring 20.

Figure 10:
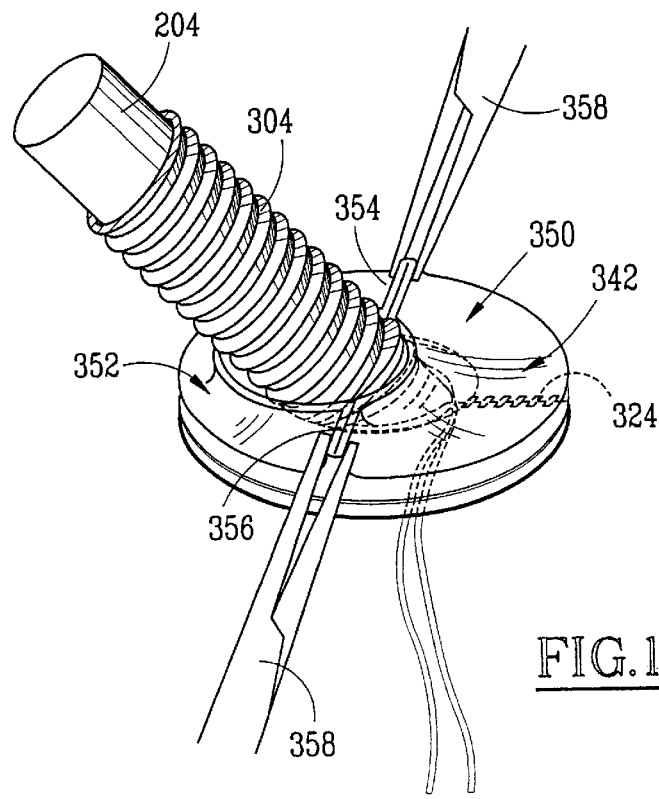
FIGS. 10 and 11 are perspective side views illustrating the next steps in the method of manufacturing the second embodiment of the prosthesis.

As illustrated in FIG. 10, the layer 342 then covers the previously exposed surface of the washer 202. It is carefully spread out by hand over the washer in two areas of application 350, 352 separated by a diameter of the disc running at right angles to the plane delimited by the axis of the rod 204 and the seam 324.

Because the layer 342 has been pressed onto the areas 350 and 352, two diametrically opposed flat folds forming bulges 354, 356 are created one on each side of the arm 304. These are held in place by clamps 358 and then the entire prosthesis which is in the process of being manufactured is subjected to a stream of steam, thus permanently marking the folds. The top ends of the bulges 354, 356 are then cut off as depicted in FIG. 10. The use of the clamps 358 allows the bulges 354 and 356 to be cut off while the layer 342 is pressed satisfactorily against the washer 202.

Figure 11:
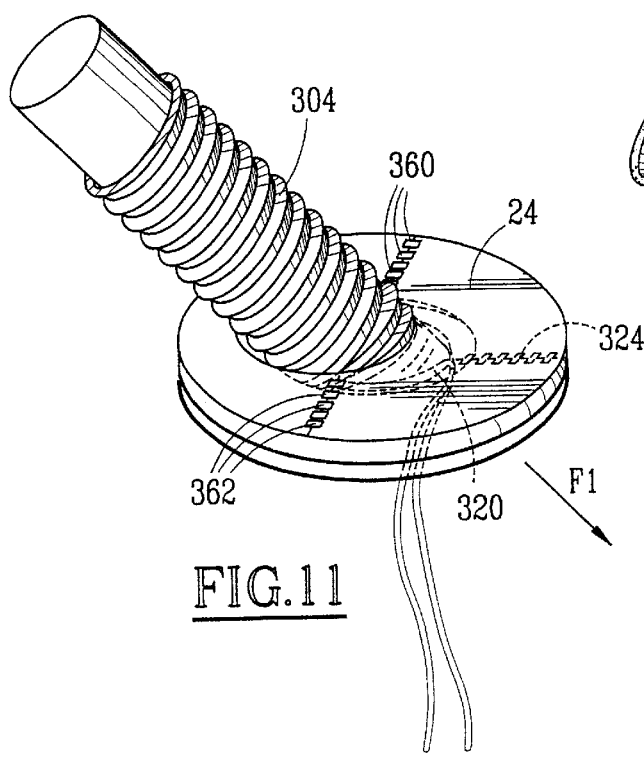

Finally, as depicted in FIG. 11, once the clamps have been removed, the edges of the layer 342, defined when the folds 354 and 356 were cut off, are sewn together with hand-stitched seams 360, 362.

These seams run along one and the same diameter of the disc 206, which runs roughly at right angles to the seam 324.

Thus, after the joints have been made, the second ring 24 is formed above the washer 204.

In order to obtain the finished flanged prosthesis, the thread 320 is removed and the tool body 200 is disengaged in the direction of the arrow F1 in FIG. 11. Through deformation of the flange formed of the rings 20 and 24, the washer 202 is finally extracted and disengaged from the tubular body 18.

Figure 12:
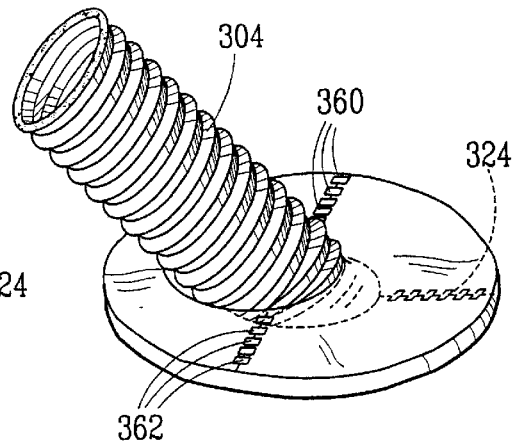
FIG. 12 is a perspective view of the second embodiment of the prosthesis when it is finished.

The flanged prosthesis thus separated from the tool is depicted alone in FIG. 12.

At the end of the manufacturing steps described previously, the prosthesis is finally completely coated with a suitable collagen, according to a technique known per se.

The prosthesis described here can be made of textile elements of any suitable nature, whether these be woven or knitted.

What is claimed is:

1. A flanged prosthesis comprising a tubular body equipped at one end with an external flange designed for anastomosis of the prosthesis to a tubular duct equipped with an opening, wherein said flange is formed of a textile material and further comprises a first ring having an inner periphery and secured, around said inner periphery, to said end of said tubular body, wherein said first ring is formed integrally with said tubular body, wherein said first ring comprises a transverse seam which shapes said flange at said end of said tubular body, wherein said flange further comprises a second ring surrounding said tubular body and running roughly against said first ring, said first and second rings being joined together around outer peripheries thereof, wherein said first and second rings are formed integrally with said tubular body, a peripheral fold line being formed between said first and second rings, and said second ring comprises a transverse seam, and wherein said second ring further comprises another seam, said seams of said second ring running radially on each side of said tubular body, roughly along a single diameter of said second ring.

2. A prosthesis according to claim 1, wherein at least one of the said seams runs roughly radially.

3. A prosthesis according to claim 1, wherein said seam of said first ring comprises a radial single seam running roughly at a right angle to said diameter along which the radial seams formed on said second ring run.

4. A prosthesis according to claim 1, wherein said transverse seam runs roughly radially.

* * * * *